United States Patent [19]

Ninomiya et al.

[11] Patent Number: 4,933,473

[45] Date of Patent: Jun. 12, 1990

[54] PROCESS FOR PRODUCING NEOPENTYL GLYCOL

[75] Inventors: Teruyuki Ninomiya; Tomiyoshi Furuta; Seiji Kita; Yoshimi Fujii, all of Kurashiki, Japan

[73] Assignee: Mitsubishi Gas Chemical Company, Inc., Tokyo, Japan

[21] Appl. No.: 342,226

[22] Filed: Apr. 21, 1989

[30] Foreign Application Priority Data

May 25, 1988 [JP] Japan .................................. 63-125668

[51] Int. Cl.$^5$ ....................... C07C 29/14; C07C 31/20
[52] U.S. Cl. .................................... 568/862; 568/853; 568/863
[58] Field of Search ....................... 568/862, 853, 863; 562/313

[56] References Cited

U.S. PATENT DOCUMENTS 3,340,312 9/1967 Duke, Jr. et al. .................... 568/862
3,884,838 5/1975 Fleming et al. ..................... 502/313

*Primary Examiner*—Donald B. Moyer
*Assistant Examiner*—Karen E. Plue
*Attorney, Agent, or Firm*—Frishauf, Holtz, Goodman & Woodward

[57] ABSTRACT

A process for production of neopentyl glycol by hydrogenation of hydroxypivaldehyde in the presence of a Pt-Ru-W catalyst. This catalyst exhibits high activity and selectivity, and further has a long life. Neopentyl glycol is an important intermediate for use in production of a wide variety of chemicals.

17 Claims, No Drawings

PROCESS FOR PRODUCING NEOPENTYL GLYCOL

BACKGROUND OF THE INVENTION

1. Field of the Invention

The present invention relates to a process for producing neopentyl glycol. More particularly, it is concerned with a process for producing neopentyl glycol (2,2-dimethyl-1,3-propanediol) by hydrogenating hydroxypivaldehyde (2,2-dimethyl-3-hydroxy propanal) as obtained by the condensation of isobutyraldehyde and formaldehyde, in the presence of a three-component catalyst of platinum-ruthenium-tungsten (hereinafter abbreviated to "Pt-Ru-W"). 2. Description of Related Arts Neopentyl glycol is a very important intermediate for industrial use and has a wide variety of applications; for example, it is used in production of various synthetic resins such as acrylic resins, polyester resins, polyurethane resins, alkyd resins and polycarbonate resins, a plasticizer, a synthetic lubricating oil, a synthetic drying oil, a fiber processing agent, or a surfactant.

Neopentyl glycol has been usually produced by the following two methods.

In accordance with one of the methods, isobutyraldehyde and formaldehyde are subjected to an aldol condensation reaction and then to a crossed Cannizzaro reaction in the presence of a strongly alkaline catalyst, e.g. caustic soda, caustic potash or calcium hydroxide to thereby obtain the desired neopentyl glycol. This method, however, has a disadvantage in that sodium formate is also produced in an equimolar amount to the desired product. Therefore, unless sodium formate is effectively utilized, the method is unsuitable for use in production of neopentyl glycol on a commercial scale.

In accordance with another method, hydroxypivaldehyde, as obtained by the reaction of isobutyraldehyde and formaldehyde, is hydrogenated in the presence of a catalyst to thereby produce the desired neopentyl glycol, which is not accompanied by the production of sodium formate. This method is disclosed in Japanese Patent Publication Nos. 33169/1974, 17568/1678, U.S. Pat. Nos. 1,048,530, 1,219,162, 3,920,760, 4,021,496, West German Patent No. 1,014,089, European Patent Nos. 44,421, 44,444. In these patents, Raney nickel, Ni-Cr, Cu-Zn, Cu-Al, Cu-Cr and Cr-Ba catalysts are disclosed as catalysts for use in the hydrogenation reaction.

These conventional catalysts suffer from problems in that catalytic activity is insufficient and thus the reaction must be carried out under high pressure conditions, and that catalytic activity cannot be maintained at a high level for a long period of time since it is decreased under the influences of small amounts of impurities contained in hydroxypivaldehyde as the starting material. In the case of the Raney nickel catalyst, various problems arise; for example, preparation and handling of the catalyst are not easy, catalytic activity is insufficient and furthermore it cannot be maintained for a long time, and since the catalyst is used in a slurry form, the process inevitably becomes complicated.

SUMMARY OF THE INVENTION

As a result of investigations to overcome the above problems encountered in production of neopentyl glycol through hydrogenation of hydroxypivaldehyde, it has been found that a three-component Pt-Ru-W catalyst exhibits excellent performance in the hydrogenation reaction.

An object of the present invention is to provide a process for producing neopentyl glycol with high catalytic activity and high selectivity.

Another object of the present invention is to provide a process for producing neopentyl glycol with high productivity for a long period of time.

The present invention relates to a process for producing neopentyl glycol which comprises hydrogenating hydroxypivaldehyde in the presence of a Pt-Ru-W catalyst.

DESCRIPTION OF THE PREFERRED EMBODIMENTS

The process of the present invention usually proceeds in aqueous solvent. The aqueous solvent includes water and a mixed solvent of water and alcohol such as water-methanol, water-ethanol, water-n-propanol, water-isopropanol, water-n-butanol and water-isobutanol. Hydroxypivaldehyde to be used in the process of the present invention can be easily obtained by the aldol condensation reaction of isobutyraldehyde and formaldehyde in the presence of a basic catalyst according to the usual method. For example, the condensation reaction of formaldehyde and isobutyraldehyde is carried out at 50° to 95° C. in the presence of a tertiary amine catalyst, e.g. trimethylamine or triethylamine, or is carried out at 15° to 40° C. in the presence of a strongly alkaline catalyst, e.g. caustic soda. In the condensation reaction, the molar ratio of isobutyraldehyde to formaldehyde is 0.8:1 to 1.3:1 and preferably 1.1:1 to 1.2:1.

As hydroxypivaldehyde to be used for the starting material in the process of the present invention, the reaction mixture resulting from the above aldol condensation reaction may be used as such or after separation of unreacted isobutyraldehyde and formaldehyde. In addition, a dimer of hydroxypivaldehyde as obtained by crystallization in water after the separation of unreacted isobutyraldehyde and formaldehyde can be used the starting material. The dimer is represented by the following formula.

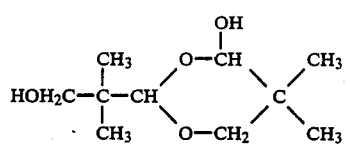

The dimer can be used in the process of the present invention without any hidrance because it acts as a hydroxypivaldehyde monomer in the hydrogenation reaction.

In accordance with the process of the present invention, hydroxypivaldehyde is dissolved in a suitable amount of aqueous solvent such as water and is subjected to the hydrogenation reaction in the presence of the Pt-Ru-W catalyst. The aqueous hydroxypivaldehyde solution may contain not more than 5.0% by weight of impurities such as unreacted isobutyraldehyde, formaldehyde and tertiary amine, amine compounds and sodium formate.

If catalysts containing Pt and Ru, singly or in combination with each other, are used, problems arise in catalytic activity and service life of the catalyst. These problems can be overcome by using the Pt-Ru-W catalyst of the present invention.

The significant effect of the catalyst in the present invention is exhibited as long as Pt, Ru and W are present even if the relative proportion of one element is small. The preferable catalyst composition is such that the weight ratio of Ru to Pt is 0.1:1 to 10:1 and preferably 0.2:1 to 5:1 and the weight ratio of W to Pt is 0.005:1 to 5:1 and preferably 0.01:1 to 2:1.

As the starting materials for preparation of the catalyst of the present invention, inorganic acid salts of the above elements, e.g. chloride, nitrate, sulfate and carbonate; oxides; hydroxides; organic acid salts; oxyacid salts; carbonyl compound and complexes can be used.

Any method can be employed in preparation of the catalyst of the present invention as long as in the final catalytic state, the elementary combination and the atomic ratios are satisfied with the requirement described above, and the catalyst is in the state durable for practical use. A catalyst support can or can not be used.

A convenient method for preparing a catalyst deposited on a support will hereinafter be explained.

An aqueous mixture into which chloroplatinic acid, ruthenium trichloride and ammonium tungstate has been dissolved in a predetermined ratio, is added to a catalyst support. Water is evaporated by heating while stirring. The residue is dried at a temperature of about 120° C. and then calcined at decomposition temperatures of the salts used.

Supports which can be used in the present invention include silica, alumina, silica-alumina, zeolite, magnesium oxide, titanium oxide, zirconium oxide, diatomaceous earth, carbon, silicon carbide, and the like.

When a catalyst support is used, the amounts of the catalyst components, Pt, Ru and W, deposited on the support are each within the range of 0.005 to 10 wt% (calculated as metal), with the range of 0.01 to 5 wt% being particularly effective, although they vary with the kind of the support. The catalyst components can be deposited on the support by any suitable method such as a method in which the three catalyst components are deposited on the support at the same time or a method in which each of the catalyst components are deposited successively. In addition, irrespective of the presence or absence of the catalyst support, depending on the kind of the compound to be used, there can be employed a method in which an aqueous solution of the component mixture is neutralized with a suitable acid or base to precipitate a mixed metal salt, which is then filtered, washed and dried and, thereafter calcined, or when water-insoluble compounds are used, there can be employed a method in which a uniform slurry of the components is prepared, and then dried and calcined.

The catalyst of the present invention can be used in a powder form or a tablet form obtained by compression molding. It can be employed in any reaction system such as a fixed bed system or a fluid bed system. After activation through hydrogenation and hydrogen according to the ordinary method, the catalyst is used in the hydrogenation reaction of the present invention.

The process of the present invention will hereinafter be explained in detail.

Aqueous medium, especially water, as a reaction solvent is used in such an amount that the hydroxypivaldehyde concentration is within the range of 10 to 80% by weight, preferably 15 to 60% by weight. If the hydroxypivaldehyde concentration is less than 10% by weight, it is difficult to separate neopentyl glycol formed from water, and the energy load for evaporation to dehydration increases. On the other hand, if it is more than 80% by weight, Tishchenko reaction between the hydroxypivaldehydes themselves occurs, resulting in neopentyl glycol ester of hydroxypivalic acid as by-product, which is unsuitable for practical use.

For hydrogenation reaction of hydroxypivaldehyde according to the process of the present invention, the Pt-Ru-W catalyst is dispersed or suspended in the aqueous solution containing hydroxypivaldehyde as the starting material in the presence of hydrogen, or the aqueous solution containing the starting material is passed through a column packed with the catalyst in the presence of hydrogen to produce neopentyl glycol.

The hydrogenation reaction can be carried out continuously or batchwise.

The reaction temperature is 60° to 150° C. and preferably 80° to 130° C.

The reaction pressure is 1 to 50 $kg/cm^2$ and preferably 5 to 40 $kg/cm^2$, and the pressure is maintained by introducing hydrogen.

Although the reaction can be carried out outside the above specified reaction condition ranges, it proceeds efficiently under the above reaction conditions.

Separation and recovery of the objective neopentyl glycol from the reaction mixture after completion of the reaction can be carried out by techniques such as distillation or solvent extraction.

In accordance with the process of the present invention, in production of neopentyl glycol through hydrogenation of hydroxypivaldehyde, sufficiently high catalytic activity and selectivity are exhibited, and a long and stabilized service life of the catalyst can be realized. Thus the present invention has great industrial significance.

The present invention is described in greater detail with reference to the following examples, although it is not limited thereto. All parts and percents (%) are by weight. The compound names were abbreviated as follows:

HPA: hydroxypivaldehyde,
NPG: neopentyl glycol
IBA: isobutyraldehyde,
TEA: triethylamine, and
HPNE: hydroxypivalic acid neopentyl glycol ester

EXAMPLE 1

1.5 parts of powdered HPA (purity:99.8%), 10 parts of water and 0.5 parts of a 0.4%Pt-0.3%Ru-0.01%W catalyst deposited on active carbon were placed in a 100-milliliter stainless steel autoclave, which was then closed. After thorough purging with hydrogen, hydrogen was introduced under pressure into the autoclave to maintain the hydrogen partial pressure at 9.8 $kg/cm^2$.

The autoclave was placed on an agitator. While agitating the autoclave, the reaction was carried out by raising the temperature of the contents from room temperature to 120° C. over a period of 15 minutes and then maintaining at 120° for 15 minutes by the use of an external heater.

After the reaction was completed, the autoclave was cooled to room temperature. At this time, the pressure was decreased to 5.2 $kg/cm^2$.

After separation of the catalyst, 11.5 parts of a reaction solution was obtained. A gas chromatographic analysis showed that the reaction solution had the following composition:

HPA: 0%,
NPG: 13.26%,
HPNE: 0%,

H₂O: 86.74%.

The conversion of HPA was 100%, and the selectivity into NPG was 100%. Thus it can be seen that the objective product could be obtained quantitatively.

EXAMPLES 2 TO 11

In the same manner as in Example 1 except that the recovered catalyst was used repeatedly, HPA was hydrogenated under the reaction conditions shown in Table 1.

As a result, NPG was quantitatively obtained as shown in Table 1.

TABLE 1

| | | Charging Conditions | | | | Reaction Conditions | | Results | |
|---|---|---|---|---|---|---|---|---|---|
| No. | Repeating Number | HPA (g) | Water (g) | Amount of Catalyst (g) | H₂ Partial Pressure (kg/cm²) | Temperature (°C.) | Time (min) (raising time/ maintaining time) | HPA Conversion (mol %) | NPG Selectivity (mol %) |
| Example 2 | 1 | 2.1 | 16.9 | 2.0 | 40.0 | 95 | 25/45 | 100 | 10 |
| Example 3 | 2 | 4.1 | 25.0 | 2.0 | 25.0 | 85 | 40/20 | 100 | 10 |
| Example 4 | 3 | 1.5 | 10.0 | 1.0 | 9.9 | 120 | 15/30 | 100 | 10 |
| Example 5 | 4 | 1.5 | 10.0 | 0.5 | 8.5 | 120 | 10/20 | 100 | 10 |
| Example 6 | 5 | 1.5 | 10.0 | 0.5 | 8.8 | 120 | 15/25 | 100 | 10 |
| Example 7 | 6 | 4.0 | 23.4 | 2.0 | 25.0 | 110 | 30/15 | 100 | 10 |
| Example 8 | 7 | 4.1 | 25.7 | 2.0 | 25.0 | 80 | 30/18 | 100 | 10 |
| Example 9 | 8 | 1.5 | 10.0 | 1.0 | 9.8 | 120 | 15/25 | 100 | 10 |
| Example 10 | 9 | 2.0 | 16.6 | 2.0 | 40.0 | 90 | 25/60 | 100 | 10 |
| Example 11 | 10 | 1.5 | 10.0 | 0.5 | 8.0 | 120 | 10/20 | 100 | 10 |

EXAMPLE 12

In a 2 liter four-necked round bottom flask equipped with a condenser, a thermometer, a nitrogen gas inlet nozzle and stirrer, 595 parts of IBA, 657 parts of 37% formalin and 33 parts of TEA were added through the dropping funnel over a period of 10 minutes while stirring at 30° C. in a nitrogen stream. The temperature of the reaction mixture rose to 60° to 65° C. in 7 to 8 minutes, and within the range of 65° to 73° C., IBA vigorously reflexed for about 10 minutes.

At the point that the refluxing was coming to an end, heating with an external heater was started, and when the temperature of the reaction mixture reached 90° C., the reaction was stopped. Twenty minutes were required for this process, and 1,285 parts of a reaction solution was obtained. This solution was diluted with an equal amount of water to prepare a solution to be hydrogenated.

The results of a gas chromatographic analysis of the solution to be hydrogenated are shown in the left column of Table 2.

TABLE 2

| Components | Solution to be Hydrogenated | (Unit: %) Hydrogenated Solution |
|---|---|---|
| HPA | 31.2 | 0.1 |
| IBA | 0.4 | trace |
| TEA | 0.9 | trace |
| CH₃OH | 0.8 | 0.9 |
| HPNE | 1.2 | 1.7 |
| Water | 63.2 | 63.4 |
| Unknown | 1.7 | 3.5 |
| NPG | 0.6 | 30.4 |

The hydrogenation reaction was carried out as follows.

200 parts of the above solution and 20 parts of a 0.9% Pt-0.5%Ru-0.01%W catalyst deposited on active carbon were placed in a 0.3-liter stainless steel autoclave equipped with a reflux condenser, a feed introduction tube, a hydrogen introduction tube, and a stirring apparatus, and hydrogen was introduced in the autoclave at a constant hydrogen partial pressure of 8.0 kg/cm². The reaction was carried out batchwise with stirring for 40 minutes.

Then, the above solution was introduced continuously into the reaction system at a rate of 80 g/hr and at the same time hydrogen was continuously supplied while maintaining the hydrogen partial pressure at 8.0 kg/cm². Simultaneously, the reaction mixture was continuously withdrawn from the bottom of the autoclave while maintaining the liquid in the system at a constant level. The reaction was carried out under stationary conditions continuously for 25 hours to obtain 2,200 parts of a reaction solution. The results of a gas chromatographic analysis of the reaction solution are shown in Table 2. The conversion of HPA was 99.7 mol %, and the selectivity into NPG was 95.6 mol %.

EXAMPLE 13

The feed solution obtained in the same manner as in Example 12 was hydrogenated in a packed layer type reaction tube having an inner diameter of 30 mm and a column length of 500 mm. The reaction tube was packed with 300 ml of a 0.5%Pt-0.4%Ru-0.02%W catalyst deposited on active carbon. The feed solution was continuously introduced at a flow rate of LHSV (Liquid Hourly Space Velocity) about 0.7 hr⁻¹, and hydrogen was supplied simultaneously while maintaining the partial pressure at 9.5 kg/cm² by automatic control. The hydrogenation reaction was carried out continuously for 28 days. The results are shown in Table 3.

TABLE 3

| Operating Days (days) | Feed Amount (kg) | Temperature (°C.) Top Stage | Middle Stage | Bottom Stage | LHSV (hr⁻¹) | HPA Conversion (mol %) | NPG Selectivity (mol %) | Amount of NPG (kg) |
|---|---|---|---|---|---|---|---|---|
| 5 | 25.6 | 101 | 110 | 106 | 0.71 | 100 | 100 | 7.9 |

TABLE 3-continued

| Operating Days (days) | Feed Amount (kg) | Temperature (°C.) | | | LHSV (hr⁻¹) | HPA Conversion (mol %) | NPG Selectivity (mol %) | Amount of NPG (kg) |
| --- | --- | --- | --- | --- | --- | --- | --- | --- |
| | | Top Stage | Middle Stage | Bottom Stage | | | | |
| 10 | 50.8 | 105 | 110 | 107 | 0.68 | 100 | 100 | 19.3 |
| 15 | 76.0 | 103 | 118 | 116 | 0.70 | 100 | 100 | 23.4 |
| 20 | 101.6 | 100 | 109 | 107 | 0.69 | 99.7 | 100 | 31.3 |
| 25 | 127.2 | 110 | 119 | 120 | 0.73 | 99.2 | 100 | 39.2 |
| 28 | 142.6 | 109 | 120 | 118 | 0.71 | 100 | 100 | 43.9 |

Common Conditions
Catalyst: 0.5% Pt-0.4% Ru-0.02% W deposited on active carbon
Bulk Density: 0.45 g/ml
Catalyst Packed Layer: 30 mm (diameter) × 500 mm (length)
Amount of Catalyst: 300 ml
Hydrogenation Conditions: Column liquid type
Temperature (middle stage): 106 to 120° C.
Pressure: 9.5 kg/cm²
LHSV: 0.68 to 0.73 hr⁻¹

During the process, absolutely no decrease in catalytic activity was observed, and NPG was formed quantitatively.

142.6 kg of the total reaction mixture was mixed together. A 5 kg portion of the mixture was subjected to dehydration under reduced pressure in a packed column type distillation column (number of plates: 10; Sulzer pack filler produced by Sumitomo Jukikai Co., Ltd.), and subsequently, purification distillation was carried out to obtain 1.44 kg of NPG.

Dehydration and purification distillation conditions are shown in Table 4, and the quality of NPG is shown in Table 5. It was found that the NPG obtained was of high quality.

TABLE 4

| | Dehydration | Purification Distillation |
| --- | --- | --- |
| Temperature (°C.) (Top/Bottom) | 65 to 70/80 | 140 to 145/150 to 160 |
| Degree of Vacuum (mm Hg) (Top/Bottom) | 300/400 | 48/60 |
| Reflux Ratio | 4 | 2 |

TABLE 5

| Molten Color (APHA): | 5 |
| --- | --- |
| Melting Point (°C.): | 130.1 |
| Acid Content (%) (as HCOOH): | 0.001 |
| Ester Content (%): | 0.1 |
| Water Content (%): | 0.05 |
| Ash Content (%): | 0.01 |

EXAMPLE 14 TO 16

Hydrogenation was carried out in the same manner as in Example 1 except that the amount of each component deposited was changed in the Pt-Ru-W catalyst deposited on active carbon.

The results are shown in Table 6, and NPG was formed quantitatively.

TABLE 6

| No. | Deposited Amount (%) | | | HPA Conversion (mol %) | NPG Selectivity (mol %) |
| --- | --- | --- | --- | --- | --- |
| | Pt | Ru | W | | |
| Example 14 | 1 | 1 | 0.005 | 99.5 | 100 |
| Example 15 | 5 | 1 | 0.01 | 98.6 | 100 |
| Example 16 | 5 | 3 | 0.01 | 99.7 | 100 |

EXAMPLES 17 TO 21

Hydrogenation was carried out in the same manner as in Example 1 except that alumina, silica, silica-alumina, titania or graphite carbon was used as the support in the Pt-Ru-W catalyst.

The results are shown in Table 7.

TABLE 7

| No. | Support | Deposition Amount (%) | | | HPA Conversion (mol %) | NPG Selectivity (mol %) |
| --- | --- | --- | --- | --- | --- | --- |
| | | Pt | Ru | W | | |
| Example 17 | Alumina pellet | 1 | 1 | 0.01 | 97.2 | 95.5 |
| Example 18 | Silica | 1 | 1 | 0.01 | 95.3 | 91.2 |
| Example 19 | Silica alumina | 1 | 1 | 0.01 | 93.5 | 90.1 |
| Example 20 | Titania | 1 | 1 | 0.01 | 81.1 | 74.2 |
| Example 21 | Graphite carbon | 1 | 1 | 0.01 | 92.0 | 85.4 |

COMPARATIVE EXAMPLES 1 TO 3

Hydrogenation was carried out in the same manner as in Example 1 except that a catalyst comprising 0.5% Ru deposited on active carbon was used as the catalyst.

The results are shown in Table 8.

Although the selectivity into NPG at the first reaction was satisfactory, when the reaction was repeated two or three times, the selectivity into NPG dropped unsatisfactorily.

TABLE 8

| No. | Repeating Number | HPA Conversion (mol %) | NPG Selectivity (mol %) |
| --- | --- | --- | --- |
| Comparative Example 1 | 1 | 98.2 | 96.8 |
| Comparative Example 2 | 2 | 96.5 | 67.8 |
| Comparative Example 3 | 3 | 92.0 | 49.1 |

COMPARATIVE EXAMPLES 4 TO 6

Hydrogenation was carried out in the same manner as in Example 1 except that a catalyst comprising 0.5% Pt deposited on active carbon was used as the catalyst.

The results are shown in Table 9.

TABLE 9

| No. | Repeating Number | HPA Conversion (mol %) | NPG Selectivity (mol %) |
| --- | --- | --- | --- |
| Comparative Example 4 | 1 | 100 | 53.0 |
| Comparative Example 5 | 2 | 92.5 | 50.0 |
| Comparative | 3 | 97.0 | 41.0 |

TABLE 9-continued

| No. | Repeating Number | HPA Conversion (mol %) | NPG Selectivity (mol %) |
|---|---|---|---|
| Example 6 | | | |

The selectivity into NPG at the first reaction was low, and when the reaction was repeated two or three times, the selectivity dropped more.

COMPARATIVE EXAMPLES 7 TO 9

Hydrogenation was carried out in the same manner as in Example 1 except that a catalyst comprising 0.5% Pt-0.5% Ru deposited on active carbon was used as the catalyst.

The results are shown in Table 10.

TABLE 10

| No. | Repeating Number | HPA Conversion (mol %) | NPG Selectivity (mol %) |
|---|---|---|---|
| Comparative Example 7 | 1 | 100 | 97.6 |
| Comparative Example 8 | 2 | 99.5 | 91.6 |
| Comparative Example 9 | 3 | 99.6 | 63.5 |

The catalyst comprising a combination of Pt and Ru is superior in performance to those comprising Pt or Ru alone, but is inferior to the catalyst of the present invention.

What is claimed is:

1. A process for producing neopentyl glycol which comprises hydrogenating hydroxypivaldehyde or the dimer thereof having the formula

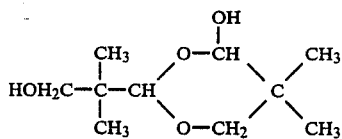

at a temperature of 60° to 150° C. and a pressure of 1 to 50 kg/cm², and in the presence of a catalyst consisting essentially of platinum, ruthenium and tungsten; the weight ratio of ruthenium to platinum is from 0.1:1 to 10:1 and the weight ratio of tungsten to platinum is from 0.005:1 to 5:1.

2. The process as claimed in claim 1, wherein the hydrogenation of hydroxypivaldehyde is carried out in aqueous solvent.

3. The process as claimed in claim 2, wherein the aqueous solvent is water.

4. The process as claimed in claim 2, wherein the aqueous solvent is a mixed solvent of water and at least one alcohol selected from the group consisting of methanol, ethanol, n-propanol, isopropanol, n-butanol and isobutanol.

5. The process as claimed in claim 1, wherein said hydroxypivaldehyde is prepared by condensation of isobutyraldehyde and formaldehyde.

6. The process as claimed in claim 2, wherein said hydrogenation is at a temperature of 80° to 130° C. and at a pressure of 5 to 40 kg/cm²; and wherein the weight ratio of ruthenium to platinum is from 0.2:1 to 5:1 and the weight ratio of tungsten to platinum is 0.01:1 to 2:1.

7. The process as claimed in claim 6, wherein hydroxypivaldehyde is hydrogenated.

8. The process as claimed in claim 6, wherein said dimer is hydrogenated.

9. A process for producing neopentyl glycol which comprises hydrogenating hydroxypivaldehyde or the dimer thereof having the formula

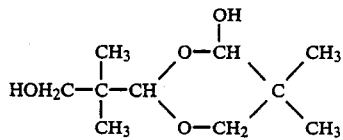

at a temperature of 60° to 150° C. and a pressure of 1 to 50 kg/cm²; and in the presence of a catalyst consisting essentially of platinum, ruthenium and tungsten on a catalyst support; the weight ratio of ruthenium to platinum is from 0.1:1 to 10:1 and the weight ratio of tungsten to platinum is from 0.005:1 to 5:1.

10. The process as claimed in claim 8, wherein the support is at least one member selected from the group consisting of silica, alumina, silica-alumina, zeolite, magnesium oxide, titanium oxide, zirconium oxide, diatomaceous earth, carbon, and silicon carbide.

11. The process as claimed in claim 9, wherein the hydrogenation is carried out in aqueous solvent.

12. The process as claimed in claim 11, wherein said hydrogenation is at a temperature of 80° to 130° C. and at a pressure of 5 to 40 kg/cm²; and wherein the weight ratio of ruthenium to platinum is from 0.2:1 to 5:1 and the weight ratio of tungsten to platinum is 0.01:1 2:1.

13. The process as claimed in claim 12, wherein said catalyst comprises platinum, ruthenium and tungsten deposited on a support which is at least one member selected from the group consisting of silica, alumina, silica-alumina, zeolite, magnesium oxide, titanium oxide, zirconium oxide, diatomaceous earth, carbon and silicon carbide.

14. The process as claimed in claim 13, wherein hydroxypivaldehyde is hydrogenated in water as a solvent and said support is active carbon.

15. The process as claimed in claim 13, wherein said dimer is hydrogenated in water as a solvent and said support is active carbon.

16. The process as claimed in claim 13, wherein said aqueous solvent is water.

17. The process as claimed in claim 13, wherein said aqueous solvent is a mixed solvent of water annd at least one alcohol selected from the group consisting of methanol, ethanol, n-propanol, isopropanol, n-butanol and isobutanol.

* * * * *